US010980506B2

(12) United States Patent
Roessl et al.

(10) Patent No.: US 10,980,506 B2
(45) Date of Patent: Apr. 20, 2021

(54) PHOTON-COUNTING COMPUTED TOMOGRAPHY

(71) Applicant: KONINKLIJKE PHILIPS N.V., Eindhoven (NL)

(72) Inventors: Ewald Roessl, Ellerau (NL); Roger Steadman, Aachen (DE); Christoph Herrmann, Aachen (DE); Roland Proksa, Neu Wulmstorf (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 297 days.

(21) Appl. No.: 16/305,529

(22) PCT Filed: Jun. 29, 2017

(86) PCT No.: PCT/EP2017/066139
§ 371 (c)(1),
(2) Date: Nov. 29, 2018

(87) PCT Pub. No.: WO2018/002226
PCT Pub. Date: Jan. 4, 2018

(65) Prior Publication Data
US 2020/0390413 A1 Dec. 17, 2020

(30) Foreign Application Priority Data
Jun. 29, 2016 (EP) .................................. 16176936

(51) Int. Cl.
A61B 6/00 (2006.01)
G01N 23/046 (2018.01)
(Continued)

(52) U.S. Cl.
CPC ............ *A61B 6/585* (2013.01); *A61B 6/4241* (2013.01); *A61B 6/482* (2013.01); *A61B 6/5258* (2013.01);
(Continued)

(58) Field of Classification Search
CPC ....... A61B 6/585; A61B 6/482; A61B 6/4241; A61B 6/5258; G01N 23/046;
(Continued)

(56) References Cited

U.S. PATENT DOCUMENTS

2010/0074397 A1   3/2010   Kappler
2015/0160355 A1   6/2015   Wang
(Continued)

FOREIGN PATENT DOCUMENTS

WO   2007/049168   5/2007
WO   2008155679    12/2008
(Continued)

OTHER PUBLICATIONS

Schirra, et al., "Towards K-edge imaging using a new semi-analytical calibration method", Progress in Biomedical Optics and Imaging, SPIE, vol. 9033, Mar. 19, 2014.
(Continued)

*Primary Examiner* — David P Porta
*Assistant Examiner* — Gisselle M Gutierrez
(74) *Attorney, Agent, or Firm* — Larry Liberchuk

(57) ABSTRACT

An image signal processing system (ISP) comprising an input interface (IN) for receiving photon counting projection data acquired by an X-ray imaging apparatus (IA) having a photon counting detector (D). A calibration data memory (CMEM) of the system holds calibration data. The calibration data encodes photon counting data versus path lengths curves for different energy thresholds of i) said detector (D) or ii) of a different detector. At least one of said curves is not one-to-one. A path length convertor (PLC) of the system converts an entry in said photon counting projection data into an associated path length based on said calibration data.

12 Claims, 7 Drawing Sheets

(51) Int. Cl.
*G01N 23/083* (2018.01)
*G06T 11/00* (2006.01)

(52) U.S. Cl.
CPC ......... *G01N 23/046* (2013.01); *G01N 23/083* (2013.01); *G06T 11/003* (2013.01); *G01N 2223/303* (2013.01); *G01N 2223/401* (2013.01); *G01N 2223/505* (2013.01)

(58) Field of Classification Search
CPC ........... G01N 23/083; G01N 2223/303; G01N 2223/401; G01N 2223/505; G06T 11/003
USPC ......................................................... 378/19
See application file for complete search history.

(56) References Cited

U.S. PATENT DOCUMENTS

2015/0182176 A1 7/2015 Jin
2017/0100085 A1* 4/2017 Roessl ...................... G01T 1/17

FOREIGN PATENT DOCUMENTS

| WO | 2014002022 | 1/2014 |
|---|---|---|
| WO | 2014181315 | 11/2014 |
| WO | 2015/197786 | 12/2015 |

OTHER PUBLICATIONS

Koenig, et al., "Imaging properties of small-pixel spectroscopic x-ray detectors based on cadmium telluride sensors", Physics in Medicine and Biology, vol. 57, No. 21, Oct. 3, 2012.

Yu, et al., "Evaluation of conventional imaging performance in a research whole-body CT system with a photon-counting detector array" in Phys. Med. Biol., vol. 61, pp. 1572-1595 (2016).

Alvarez, et al., "Energy-selective Reconstructions in X-ray Computerized Tomography", Phys. Med. Biol., 1976, vol. 21, No. 5, 733-744).

Schirra et al in "Statistical Reconstruction of Material Decomposed Data in Spectral CT", IEEE Trans on Medical Imaging, vol. 32, No. 7, Jul. 2013.

Roessl, et al. "K-edge imaging in x-ray computed tomography using multi-bin photon counting detectors", Phys. Med. Biol 52. (2007).

Roessl, et al., "Fourier approach to pulse pile-up in photon-counting x-ray detectors", Med. Phys. 43, pp. 1295 (2016).

* cited by examiner

PHOTON-COUNTING COMPUTED TOMOGRAPHY

CROSS REFERENCE TO RELATED APPLICATIONS

This application is the U.S. National Phase application under 35 U.S.C. § 371 of International Application No. PCT/EP2017/066139, filed Jun. 29, 2017 published as WO 2018/002226 on Jan. 4, 2018, which claims the benefit of European Patent Application Number 16176936.9 filed Jun. 29, 2016. These applications are hereby incorporated by reference herein.

FIELD OF THE INVENTION

The invention relates to an image signal processing system, to imaging systems, to an image signal processing method, to a computer readable medium, to a computer program element and to the computer readable medium.

BACKGROUND OF THE INVENTION

X-ray based imaging is an important tool in various fields of endeavor, such as medical.

In the medical field, more traditional X-ray systems use energy integrating detectors where the spectral information inherent in the detected x-ray radiation is essentially ignored. This situation has been improved with the advent of photon counting detector systems that are capable of resolving the energy in the detected radiation into spectral energy components to so enhance information content extraction.

The pixel size (pixel pitch) as used in photon counting detectors has an effect on the rate performance. In particular, the smaller the pixel size, the better the rate performance. A pixel size of about 200 microns is used in some photon-counting CT systems. See for instance Zhicong Yu et al's "Evaluation of conventional imaging performance in a research whole-body CT system with a photon-counting detector array" in Phys. Med. Biol., vol 61, pp 1572-1595 (2016). It is a fact that a sufficiently small pixel size in paralyzable detectors helps to prevent the otherwise unavoidable fold-over of the output-count rate as a function of input flux outside the flux range of clinical CT.

However, in such systems, weaker spectral performance is one of the consequences because of an increase in charge sharing events.

To that end, Carsten Schirra et al's "Towards In-vivo K-edge Imaging Using a New Semi-Analytical Calibration method" in Proc. of SPIE, vol. 9033, pp. 90330N-1-90330N-9 (2014) disclose a semi-analytical calibration method to be used in photon-counting spectral computed tomography which combines the utilization of calibration measurements with an analytical model to predict the expected photon counts.

WO 2015/197786 A1 discloses a method and an apparatus for processing of count events detected by an X-ray sensitive detector, whereby a signal model is used to fit the detected events to compute a physical quantity of interest, such as attenuation, refraction or decoherence/scattering power. By means of this, in particular pile-up effects may be accounted for.

WO 2007/049168 A1 discloses an apparatus that receives signals from a detector which is sensitive to ionizing radiation, whereby a differentiator generates an output indicative of the rate change of the detector signal. A discriminator then classifies the amplitude of the differentiator and an integrator triggered by the output of the discriminator generates outputs indicative of the detected photons. One or more correctors correct for pulse pile-ups and a combiner uses the outputs of the correctors to generate an output signal that is indicative of the number and energy distribution of the detected photons.

US 2010/0074397 A1 discloses a method for detection X-ray radiation and an respective X-ray system. An electric pulse of a pulse amplitude characteristic of the energy of a quantum is generated when a quantum of the X-ray radiation impinges on a sensor, wherein a number of threshold energies are predetermined. When the pulse amplitude corresponding to the respective energy is exceeded, a signal is emitted each time the pulse amplitude corresponding to a respective threshold energy is exceeded. This permits for reliable and high-quality imaging, even in image regions with high X-ray quanta rates. To this end, at least one of the threshold energies is predetermined such that it is higher than the maximum energy of the X-ray spectrum emitted by the X-ray emitter.

SUMMARY OF THE INVENTION

There may therefore be a need in photon counting systems to address some of the shortcomings mentioned above.

The object of the present invention is solved by the subject matter of the independent claims where further embodiments are incorporated in the dependent claims. It should be noted that the following described aspect of the invention equally applies to the image signal processing method, the image signal processing systems, to the computer program element and to the computer readable medium.

According to a first aspect of the invention there is provided an image signal processing system, comprising:

an input interface for receiving photon counting projection data acquired by an X-ray imaging apparatus having a photon counting detector;

a calibration data memory holding calibration data, said calibration data encoding photon counting data versus path lengths curves for different energy thresholds of i) said detector or ii) of a different detector, at least one of said curves being non-injective; and a path length convertor configured to convert an entry (that is, counts for a pixel) in said photon counting projection data into an associated path length based on at least two photon counting data versus path lengths curves encoded in said calibration data.

According to one embodiment, the calibration data was previously detected in a calibration procedure or said calibration data set derived (theoretically) from a signal model.

According to one embodiment, the system comprises an image reconstructor configured to reconstruct, based at least on the converted path length, an image element of an image.

According to one embodiment, the path length convertor operates to fit said entry of the photon counting projection data to photon counting data as per at least two of said curves.

According to one embodiment, the path length conversion by the path length convertor comprises computing at least two estimates for the associated path length based on one of the at least two curves and choosing one of the two estimates as the associated path length based i) on at least one other of the curves and photon counting projection data for at least one other threshold.

According to one embodiment, the path length convertor is configured to convert into the associated path length by optimizing an objective function, said objective function being dependent on a deviation between the projection data and photon counting data as per the curves. In particular, and according to one embodiment, the objective function combines the deviations ("mismatch") between measurements and expectation from the calibration curves for all energy bins at once.

According to one embodiment the objective function includes a least squares sum.

According to one embodiment, the objective function includes a likelihood function based on a probability density function (pdf) for the photon counting data. The pdf may be derived from a theoretical signal model or may be estimated from calibration data.

According to one embodiment, the objective function incorporates a noise modelling component configured to model for noise behavior of the detector or for the different detector. Again, the noise component (e.g., variances) may be derived from a theoretical signal model or may be estimated from calibration data.

The proposed path length converter is capable of converting into path lengths based on calibration curves that are not one-to-one. Curves that are not one-to-one are also referred to herein as "non-injective". The calibration data includes at least one curve (referred to herein also as "calibration curve") that is not one-to-one: In other words, there is ambiguity because there is at least one photon count value to which there are assigned, under this calibration curve, two or more different path lengths. In yet other words, the calibration curve is not invertible in the classical sense because of this ambiguity. If the curve is continuous (as will be the case when the calibration curve is interpolated or is derived from a theoretical signal model), then the non-injective curve envisaged herein may also be said to be non-monotonic.

The path length converter converts photon count data into (effective) path lengths for a given pixel, based not only on one calibration curve per threshold, but on a plurality of calibration curves for different energy thresholds (or "bin").

Said differently, the conversion operation is not restricted to operate, for a given pixel, on one curve from a given bin but other curves from other bins are also considered to implement the conversion. In one embodiment, but not necessarily all embodiments, all curves from all bins are used in the conversion for a given pixel location. The effective path length per pixel (also referred to herein simply as "path length") is computed so that its associated count rate (as per the calibration data) "best" explains some or all of the actually measured count rates in the other bins. In one extreme embodiment, only two calibration curves are considered which may indeed be sufficient in some low noise settings. Preferably however, more than two curves (3, 4 or more up to the total number of energy bins realized), in particular all curves, are included to compute the conversion for any given pixel. Using more than one calibration curve from different bins allows for more noise robust conversions, i.e. optimal estimates of the effective path length.

The proposed system allows in particular processing photon counting data from photon counting detectors with relatively large pixel size. In more detail, the proposed system allows increasing spectral performance in large pixel size detectors whilst essentially maintaining rate performance for at least some pixel positions and/or projection directions. In particular, in CT, the system ensures a favorable tradeoff between rate performance versus spectral performance given by the rate performance distribution on the sinogram. We propose herein to increase pixel size and deliberately abandon a demand for all calibration curves to be one-to-one for all pixel positions/projection directions and each bin. We thereby help secure or even increase spectral performance in particular away from a periphery of the field of view. Although rate performance for pixels at the periphery of the field of view may be compromised, spectral performance for pixels away from the periphery (in particular at center portions of the field of view) is secured.

The way in which the calibration curves are encoded may differ from embodiment to embodiment. In one embodiment the curves are simply stored as tables, in particular as look-up tables. In other embodiments, the curves are encoded as explicit functional expressions obtained by deriving same from theoretical signal models or by running an approximation scheme (in particular interpolation schemes such as polynomial or non-polynomial fitting) through the discrete set of measured calibration data points.

It will be understood that the non-injective/non-monotonic curves may still include monotonic/injective sections. More particularly, the calibration curves used are non-monotonic/non-injective at least over one interval along the path length axis.

It will be further understood that the proposed optimization implemented by the path length converter may not necessarily return a global minimum. In particular, the optimization may return a local minimum rather than a global one. Also, the optimization procedure may also be aborted after a few iterations if implemented as an iterative scheme and the output may not even constitute a local minimum but may be considered in a different context as a sufficient approximation for a local or global minimum. It will also be understood that the optimization may be formulated as a minimization or a maximization scheme. It will be understood herein that "optimization" as used herein includes a scheme that is known to converge to a local or global minimum or maximum without actually necessarily attaining it in the optimization and that the output, that is the path length, may constitute a sufficient approximation to these local or global minima or maxima. According to another aspect there is provided an X-ray imaging apparatus comprising a signal processing system of any one of the previous embodiments.

According to one aspect, there is provided an X-ray imaging apparatus comprising a photon-counting detector and an X-ray source, the source operable during imaging at a photon flux rate so that a reciprocal thereof is approximately equal to or exceeds the inverse of a dead-time of the detector. The proposed image signal processing system allows operating such an imager to produce good quality path length data.

According to another aspect, there is provided a signal processing method, comprising:

receiving photon counting projection data acquired by an X-ray imaging apparatus having a photon counting detector; and converting an entry in said photon counting projection data into an associated path length based on calibration data, said calibration data encoding photon counting data versus path lengths curves for different energy thresholds of i) said detector or ii) of a different detector, at least one of said curves being non-injective, wherein the converting is based on at least two photon counting data versus path lengths curves encoded in said calibration data.

According to one embodiment, the method comprises:

reconstructing, based at least on the converted path length, an image element of an image.

According to another aspect, there is provide a computer program element, which, when being executed by a processing unit is adapted to perform the steps of the method.

According to another aspect, there is provided a computer readable medium having stored thereon the program element.

The proposed system and method is mainly envisaged for high-flux-photon counting system such as CT or other rotational X-ray imaging system although application to non-rotational systems is also envisaged.

The photon flux rates envisaged herein are in the order of up to 300-1000 Mcps ("Mega-counts-per-second") per $mm^2$, but this is not necessary limiting herein. In one embodiment, these count rates correspond to anywhere between 50-160 MHz per pixel, depending on pixel size. Detector dead times envisaged herein are in the range of 10-50 ns.

Herein, the terms "threshold" and "bin" are being used interchangeably herein with the understanding that "bin" does not necessarily imply two-sided thresholds but in fact also includes one-sided bins in preferred embodiments where there are different single thresholds for the various energy level. One-side binning is the preferred embodiment envisaged herein for high flux settings.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
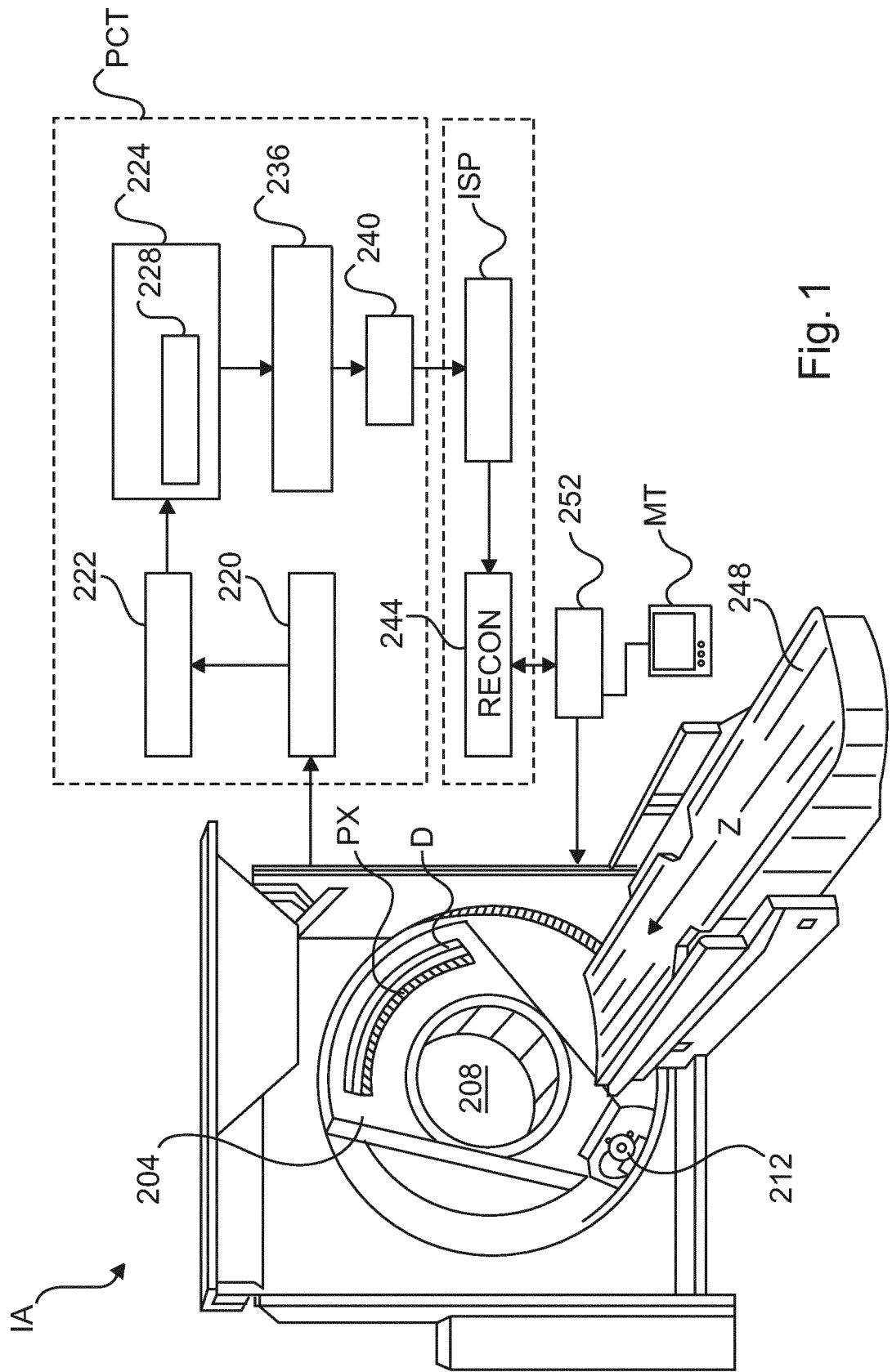
FIG. 1 shows a block diagram of an x-ray imaging apparatus.

With reference to FIG. 1, there is shown a spectral imaging arrangement 100. The spectral imaging arrangement includes in one embodiment (but not necessarily all embodiments) a computed tomography (CT) system having a rotatable gantry portion 204 that is rotatable about an examination region 208 around a longitudinal or z-axis.

An x-ray source 212, such as an x-ray tube, is supported by the rotating gantry portion 204 and emits a multi-energetic radiation beam or photons that traverse the examination region 208 from different projection directions whilst the gantry is in rotation.

An X-radiation sensitive detector D includes one or more sensors or pixels px. Each pixel px is capable of detecting photons emitted by the source 212 that traverse the examination region 208. Broadly, each pixel px generates electrical signals, such as electrical currents or voltages, which are indicative of the respective detected photons. This detection process will be described in more detail below. Examples of suitable detector systems D include direct conversion detectors, for instance detectors that include a semiconductor wafer portion or body such as a strip, typically formed from Silicon, Cadmium Telluride (CdTe) or Cadmium Zinc Telluride (CZT). Other options, often referred to as indirect conversion sensors, are also envisaged. Indirect conversion detectors are scintillator-based, that is, they include in addition a scintillator in optical communication with a photosensor. However direct conversion detectors are preferred herein.

An object support 248 such as a couch supports a patient or other object in the examination region 208. The object support 248 is movable so as to guide the object within respect to the examination region 208 when performing a scanning procedure. A general purpose computer serves as an operator console 252. The console 252 includes a human readable output device such as a monitor or display and an input device such as a keyboard and mouse. Software resident on the console 252 allows the operator to control and interact with the scanner 200, for example, through a graphical user interface (GUI). Such interaction may include instructions for reconstructing the signals based on energy-binned data as will be explained in more detail below.

During an imaging session, a specimen (a human or animal patient or parts thereof or any other object of interest (not necessarily organic)) resides in the examination region 208. The multi energetic radiation beam having an initial spectrum passes through the specimen. In its passage through the specimen the radiation interacts with matter in the specimen and is as a result of this interaction modified. It is this modified radiation that exits the patient and is then interacting with the detector pixels to produce a corresponding electrical signal. A number of physical processes operate to bring about the change or modification of the radiation in its passage through the matter of the specimen. Notable among those physical processes are absorption, refraction and de-coherence (small angle scattering or dark field effect). Each of those physical processes can be described by related physical quantities, for instance the local absorption co-efficient μ, the local refraction index φ, and a small angle scattering power Ω. The mentioned physical quantities, for instance the absorption co-efficient μ is local, that is, it differs in general across the specimen at each point thereof. More particularly the absorption is a function of the type of material (fat, bone or other material) and the density thereof at that point. Furthermore, there is also an energy dependence of the absorption μ. Alvarez and Macovski have written extensively on this (E.g, See "Energy-selective Reconstructions in X-ray Computerized Tomography", PHYS. MED. BIOL., 1976, VOL. 21, NO. 5, 733-744).

In the following, only the absorption μ is of interest. It is known that the attenuation or absorption coefficient μ varies with the energy in a manner that is characteristic of the elemental composition of the material. In other words, the x-ray energy spectrum as emitted undergoes a characteristic "coloring" during its passage through the object. One can also express the overall attenuation through the specimen along a path as a linear combination of material specific attenuation coefficients and the respective line integrals through the respective material in the specimen. See eq. (1), p 1250 in C Schirra et al in "Statistical Reconstruction of Material Decomposed Data in Spectral CT", IEEE Trans on Medical Imaging, vol 32, No 7, July 2013. Or earlier reference to Roessl et al. Phys. Med. Biol 52. (2007), eq. 3 page 4682. It is these facts that one tries to harness in spectral CT imaging to arrive at distinctive images for each of the material basis elements of interest and the overall task is to resolve the detected signals into the various material specific line integrals. In other words, the electric signals detected at the detector are spectrally analyzed ("binned") in in terms of energy bins (different energy intervals), a manner to be described in more detail below.

The spectrally processed data is then forwarded to the next stage, the image signal processing stage ISSP. This includes a re-constructor RECON. The reconstructor RECON operates to reconstruct the processed data into characteristic images for each of the different materials. In other words, an elemental decomposition is achieved as reconstructor RECON selectively reconstructs the signals generated by the detector D, based on the spectral characteristics of the detected photons. For example, the binned data can be used to generally isolate different types of organic materials having different photon absorbing characteristics such as bone, organic tissue, fat and/or the like, locate contrast enhancement materials, and/or otherwise process the detected signals based on spectral characteristics. Because the specimen is exposed to radiation across different projection directions during the rotation of the x-ray source a cross sectional representation of the interior in respect of the material of interest can be reconstructed.

Referring now to the spectral processing in more detail, the energy spectrum information is extracted through a pulse height analysis (PHA). The PHA is implemented in the FIG. 1 embodiment via a photon counting circuitry PCT of the image detection stage. The photon counting circuitry PCT is coupled to a semiconductor body CM of the detector unit D. The PCT circuitry interacts with the various detector pixels px. Each of the photons of the modified x-ray beam has a specific energy. Simply put (in particular neglecting for the moment stochastic aspects due to pile-up effects), this energy can be related in direct proportion to a magnitude (of pulse height) of an electrical pulse, caused by said photon when interacting with the detector unit D.

Figure 2:
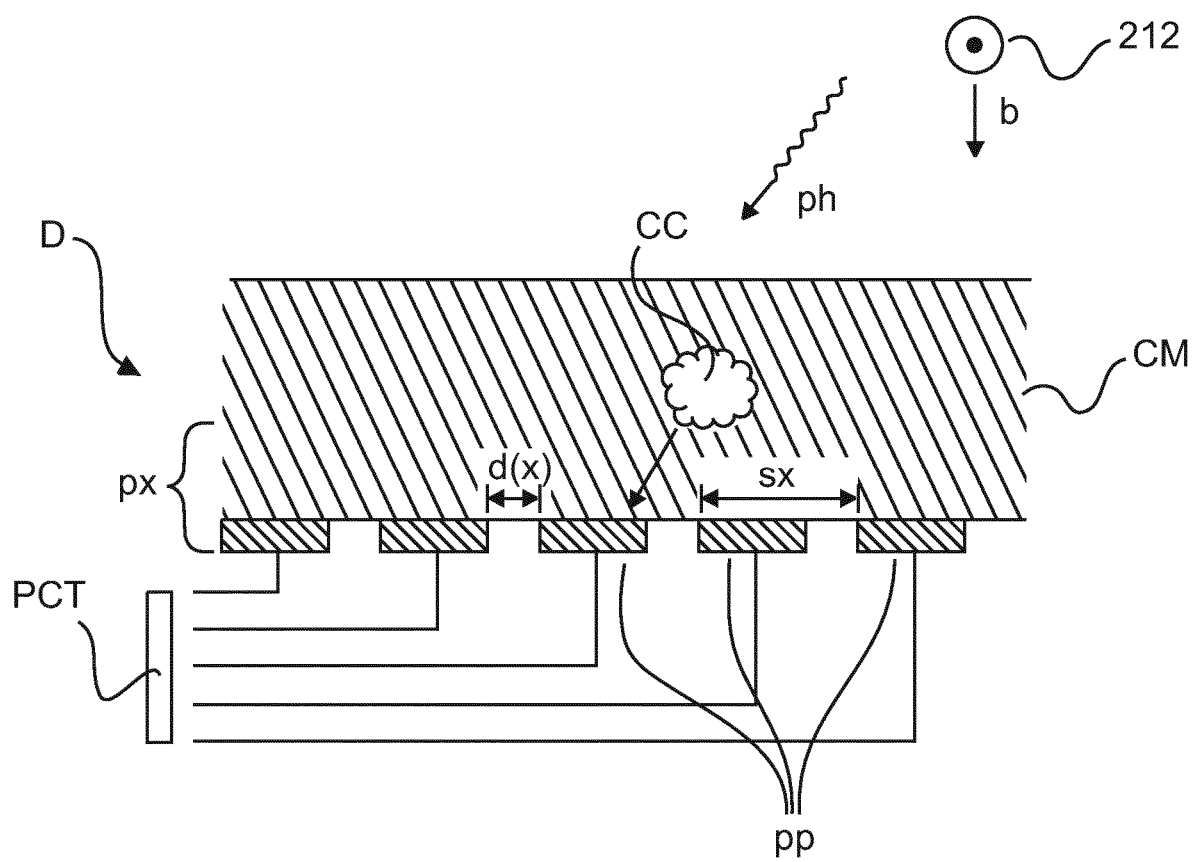
FIG. 2 shows a cross sectional view across an x-ray detector.

Before providing more details on the PCT circuitry, reference now is made to FIG. 2 to explain the photon detection operation of the detector unit D in more detail. FIG. 2 affords a sectional view across the detector D in a section plane perpendicular to the x-ray radiation sensitive surface of the detector D. The detector comprises the semiconductor body CM formed from a suitable semi-conductor material, preferably (highly) depleted of free electrons and holes. The semi-conductor material detector body CM comprises a proximal surface that is proximal to the X-ray source 212 and, opposite this surface on the other side of the body CM, a distal surface distal (further away) from the x-ray source 212. A plurality of pixel electrode pads PP is arranged on the distal surface. Respective portions in the body CM opposite the respective pads PP form together with the pads PP a respective detector pixel (or "pixel" for short). The pixels have a certain pixel pitch sx (also referred to herein as "pixel size") and are usually arranged in a grid pattern along intersecting lines ("rows and columns") on the distal surface of the semi-conductor body CM. Only one line (e.g. row) of pixels is shown in sectional FIG. 2 whilst the other lines (e.g. "columns") extend into the drawing plane of FIG. 2. For the sake of completeness, there are also anode (pad) gaps dx. It will be understood that the anode gaps dx and the pixel pitch sx may not necessarily be the same throughout the detector surface.

One or more cathodes (not shown) across the body are arranged at the proximal surface of the semi-conductor body CM. A voltage is applied across the body CM between the proximal side electrode(s) and the pixel electrodes. In operation, a photon ph of the impinging x-ray beam penetrates into the semi-conductor CM body and causes a charge cloud CC of electron-hole pairs. Under the influence of the electric field, these drift away towards the pixel electrodes by the bias voltage to cause an electric pulse which can be picked up at one or more of the pixel electrodes.

It is these electrical pulses at the detector pixels px which are processed by the photon counting circuitry PCT. To this end, each pixel electrode is coupled by an individual signal line (or "channel") with the photon counting circuitry to deliver its charge thereto. The height of the electric pulse detected at a given pixel px is a function of the impacting photon's ph energy. The higher the photon energy, the higher the pulse magnitude that can be detected at the respective pixels px.

According to one embodiment, the electrical pulses generated at the pixels px is processed by the photon counting circuitry PCT in the following manner:

A pre-amplifier 220 amplifies each electrical signal generated by any of pixels 218.

A pulse shaper 222 processes the amplified electrical signal for a detected photon and generates a corresponding analog signal that includes a pulse such as a voltage or other pulse indicative of a detected photon. The so generated pulse has a predefined shape or profile. In this example, the pulse has peak amplitude that is indicative of the energy of the detected photon.

An energy-discriminator 224 energy-discriminates the analog pulse. In this example, the energy discriminator 224 includes a plurality of comparators 228 that respectively compare the amplitude of the analog signal with a respective threshold that corresponds to a particular energy level. Neighboring threshold define an energy bin. Said differently, discriminator 224 operates to determine "height" of the incoming pulses as generated by shaper 222. More specifically, each comparator 228 produces an output count signal that is indicative of whether the amplitude of the pulse exceeds its threshold. In this example, the output signal from each comparator produces a digital signal that includes a transition from low to high (or high to low) when the pulse amplitude increases and crosses its threshold, and from high to low (or low to high) when the pulse amplitude decreases and crosses its threshold.

In an exemplary comparator embodiment, the output of each comparator transitions from low to high when the amplitude increases and crosses its threshold and from high to low when the pulse amplitude decreases and crosses its threshold.

A counter 236 counts the rising (or in some embodiments the falling) edges respectively for each threshold. The counter 236 may include a single counter or individual sub-counters for each threshold. Optionally, in case of two-sided bins only, there is an energy binner 240 that energy-bins or assigns the counts into energy ranges or bins corresponding to ranges between the energy thresholds. In fact, in the preferred embodiment with high flux, there is no binning operation into ranges but it is purely the counts of threshold crossings (i.e., one-sided binning) that are being registered.

The count data (denoted herein as $\Pi$, as described in more detail further below) may then be used to energy-resolve the detected photons. Said differently, the PCT signal processing chain operates to quantize the pulse height of each incoming pulse into the energy bins defined by the number of voltage thresholds. K (K≥2) (voltage, amperage or other physical quantity indicative of energy) thresholds are capable of defining, K different energy bins for recording pulse heights higher than respective ones of said threshold. For instance, a pulse whose edge rises beyond (that is "crosses") two of said thresholds will elicit a count for each of the two bins associated with the respective two thresholds. If only the lower one of the threshold is crossed, there will be only one count, etc. But this is an example only as in some embodiments only falling edges elicit counts or both, rising and falling edges elicit counts.

The PCT circuitry furnishes at its output, for each pixel px, a number of counts in each bin as recorded in unit time. These photon count rates per bin and pixel is referred to herein as projective photon counting data, which may be formally written as $\Pi=(m_1, \ldots m_K)^i$, with vectors of count rates $m_k$, whilst i denotes the respective pixel and $1 \le k \le K$ the number of energy bins used. Said differently, $m_k$ denotes the number of times (counts) per unit time that a pulse, whose height falls into bin k, has been recorded at pixel i. The counts may be normalized by the frame rate to represent the count rates, that is, counts per unit time. Normalization however is not a necessity and the proposed system may also operate on non-normalized count data. There are 2, 3 or more energy thresholds. In rotational systems such CT or C-arm, the recorded count rates may be different for different projection directions so the above notion may be supplemented with an additional index for the projection direction. In this later case, $\Pi$ forms a sinogram. Because the following is not restricted to rotational 3D imaging, we explain operation of the imaging system in relation to a given projection direction, with the understanding that this operation can be readily extended to projection count data collected for other projection directions.

It should be noted that the above described direct conversion detector D and the PCT circuitry are each merely exemplary embodiments, not necessarily limiting, with other constructional variants explicitly envisaged herein as alternative embodiments, so long as they output the above described projective photon counting rates $\Pi$ in whatever format.

Before explaining the system further, it may be useful to briefly introduce some concepts and related physical/technical effect that have a bearing on the functioning of the image processing system. In relation to the detection mechanism it has been observed that it is possible for the charge cloud to be detected not only by a single pixel electrode but by a plurality of (mostly neighboring) pixel electrodes. This effect is called "charge sharing". Charge sharing degrades the spectral performance and this degradation is increasing with decreasing pixel size as the size of the charge-cloud relative to the pixel size increases. Another effect is pulse-pile-up where the timing resolution of the PCT read-out electronics is insufficient to resolve the detected electric signals as separate pulses. Related to this is the so called "dead time" of the detector system. This is the time required to pass from an earlier photon count for the counting system PCT to be able to register a new, subsequent count. Said differently, a photon event that occurs before expiry of the dead-time period trigged by a former event will not be registered independently from the latter to the point where its registration will be falsified or it will not be registered at all as independent event. Such a "premature" photon counting event that occurs before expiry of the dead-time may in fact cause the dead-time to be triggered to run anew. The counting circuitry may thus be called "paralizable".

As briefly mentioned above, the detected projective photon counting data $\Pi$ is forwarded to image signal processing system ISP configured for reconstructing the projection data $\Pi$ into cross-sectional image(s) of the image domain, using any one of a range of different reconstruction algorithms such as (filtered)-back-projection, iterative reconstruction schemes (algebraic or statistical) or others.

The reconstructor component RECON cannot operate, as such, directly on the measured projective counting data $\Pi$. The image signal processing system ISP comprises a path length converter PLC configured to convert, for each pixel position, the respective count rates in one or more (preferably all) bins into a path length value for said pixel position. It is the converted into path lengths per pixel which are forwarded to the reconstructor RECON to reconstruct these into a cross-sectional image.

To better motivate and explain the operation of the proposed path length convertor PLC in more detail, it may be helpful to first introduce relevant concepts to describe performance of photon counting systems in general. Specifically, the performance of the photon counting imaging system can be characterized by rate performance and spectral performance. The rate performance can for example be quantified by the percentage of photon count events affected by pulse-pileup. The spectral performance can be quantified by the detector D's response function or by the amount of noise in material basis images.

Figure 3A:
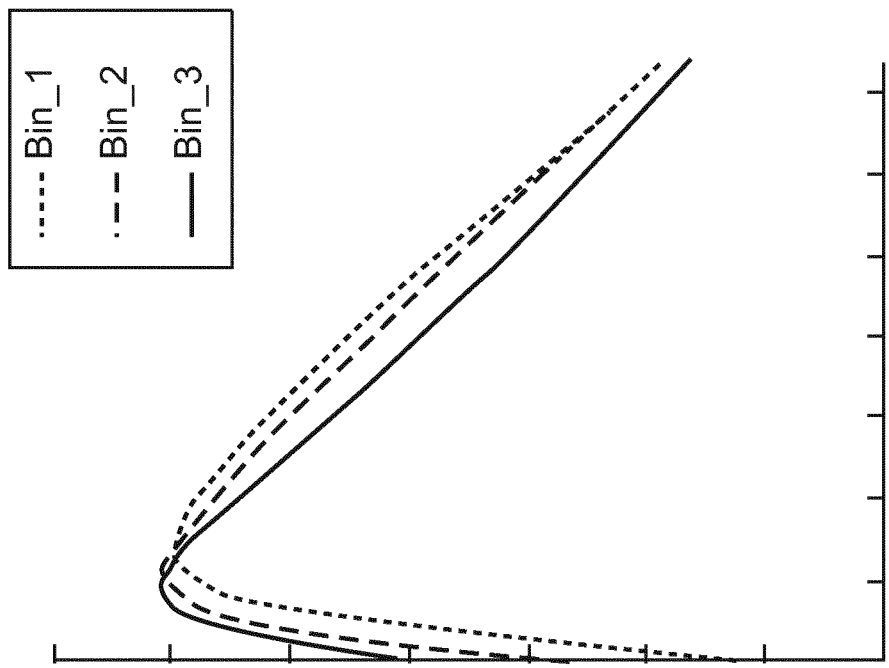
FIG. 3 shows calibration data for an x-ray imaging system.
Figure 3B:
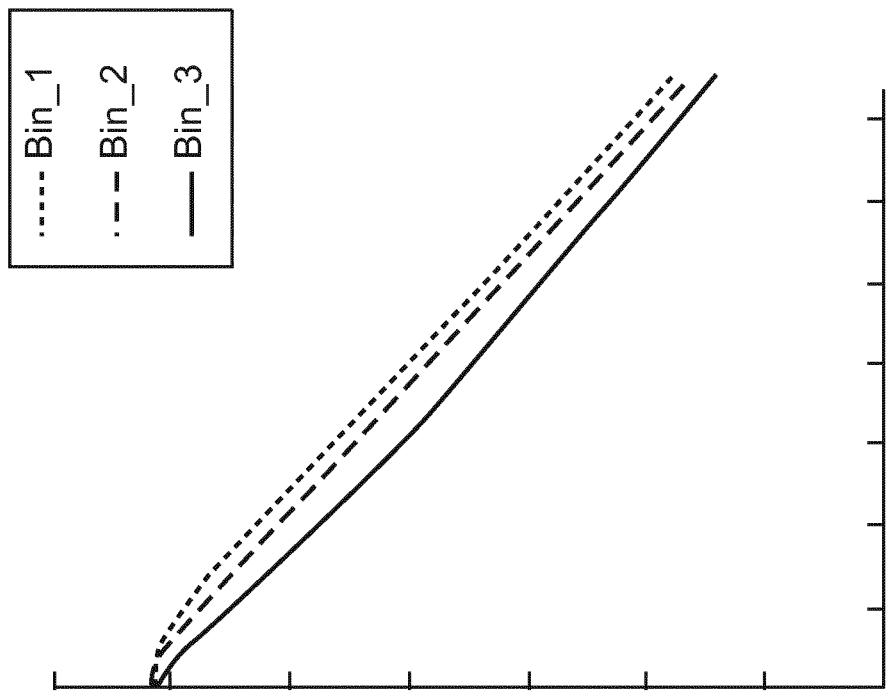

These two performance characteristics are functions of the size of the detector pixel. More specifically, the smaller the pixel size s(x), the higher in general the rate performance but the lower the spectral performance. FIG. 3 shows this in more detail. More particularly FIG. 3, shows for an arbitrary pixel position, simulations of logarithmic output count rates as a function of absorber thickness for different (e.g., K=3) energy thresholds/bins at different keV values, respectively for different pixel geometries as per pitch s(x). The curves in FIG. 3a) represent the case for small pixel pitch whereas FIG. 3b) represent the case for a larger pixel pitch. Both cases correspond to the same dead time of the detector system.

As exemplary shown in FIG. 3 the smaller, pixel pitch configuration (FIG. 3a) totally avoids the functional ambiguity of registered counts in any given single energy bin as a function of x-ray flux as compared to the non-injective curves for the larger pitch configuration (FIG. 3b). For such larger pixel pitch configurations and small attenuation lengths, significant pileup occurs. The increase in charge sharing is a necessary consequence and limits the spectral performance of a design with small pixel.

The count rates registered at the respective pixels is a function of the material (e.g., tissue) path length along which the detected photons travelled prior to their impinging the semi-conductor material CM of the detector D. The curves in FIG. 3 show this count-versus-path length relationship. These curves are not only a function of the respective energy bin but also of the inter-pixel distance/pixel size and the flux rate used. What is proposed is to make use of the fact that the curves in FIG. 3 (b) allow to determine the effective attenuation length, despite the ambiguity that exists for each individual curve. This is based on the observation that the respective maxima of the output count rate curves (FIG. 3b) depend on the energy threshold and occur at different absorber thicknesses. It has been discovered by Applicant that this very observation can be harnessed to allows designers of photon counting X-ray imaging systems (e.g. CT or others) to approach the choice of pixel size more liberally, that is, to use larger pixel sizes. This in turn enables the reconstruction of CT images with significantly larger pixels and hence much improved spectral performance whilst rate performance still remains acceptable.

It is proposed herein to measure the count rate-versus-path length curves first (referred to herein as calibration curves) for different energy bins of the imager IA in a calibration procedure and to store these in a calibration memory CMEM as calibration data. The path length converter module PLC then operates to compute from the measured photon counts Π based on the calibration data a respective path length which may then be forwarded in one embodiment to the reconstruction module RECON to perform a reconstruction.

The pixel size and/or the photon flux used is so configured that non-injective calibration curves are obtained, similar in shape to the ones shown in FIG. 3b. Not necessarily all calibration curves are non-injective. Preferably, the photon-flux is given, and the pixel size sx is the design parameter so chosen such that at least one (possibly all) calibration curve is not one-to-one. Alternatively or in addition, one may set one or more of the thresholds in the PCT circuitry high enough so as to achieve that at least one of the curves is still one-to-one. Having one (or more) one-to-one curves and at least one curve that is not one-to-one can be exploited algorithmically as will be explained further below.

Figure 4:
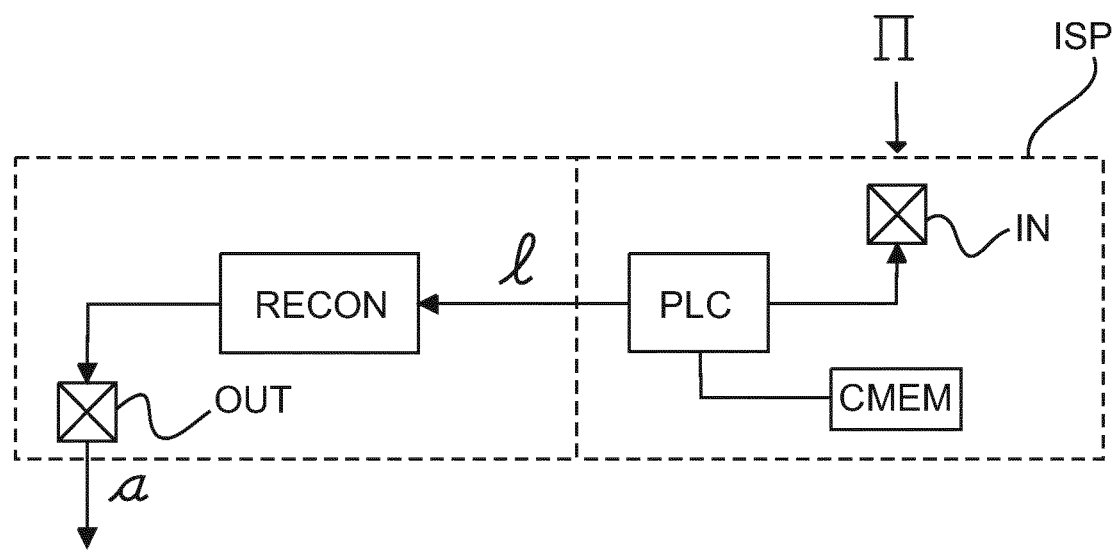
FIG. 4 shows an image signal processing stage as used in the x-ray imaging system of FIG. 1.

Components of the image signal processing stage ISP are shown in more detail in block diagram FIG. 4. The projection data Π is receivable at input port IN of the signal processing stage ISP. Π is then processed by path length converter PLC to produce respective path lengths for respective pixel positions, based on the calibration data in memory CMEM. These path lengths are returned in millimeters of effective calibration material for instance, or in any other suitable length unit. In a rotational imaging setting (such as CT or X-arm), the path lengths are forwarded to the reconstruction unit RECON to reconstruct a cross-section image for the path lengths data $\ell$. The reconstructed imagery is then output at output port OUT and these can be further converted into attenuation values such as Hounsfield units or other. The reconstructed imagery can then be stored in an image repository (e.g. PACS or other memory) or is otherwise processed such as visualized by visualizer 252 on monitor MT. The above path conversion processing by convertor PLC is understood to be repeated for each projection direction as the registered count rate photon counting projection data π is in general different for different projection directions. Although computed tomography or the rotational imagery imaging such as in computer tomography CT or C-arm/U-arm systems are preferable embodiments, this is not to the exclusion to fixed gantry radiography systems. In this later embodiment, there is no reconstruction stage RECON. The converted path lengths $\ell$ images may then be directly visualized, stored or otherwise processed. However, it will be appreciated that conversion into effective path length is merely one aspect of imaging with multi-bin photon-counting detectors as this allows producing imagery similar or "close" to conventional CT imagery. For spectral imaging tasks other processing steps such as decomposition of the image signals into different base material images are of course not excluded herein and can be independent of the path-length conversion or can build on it.

As mentioned earlier, the calibration data can be obtained in the calibration procedure. To this end, a test body (phantom) is placed on the detector and is exposed to X-radiation from the tube 212 of the imager at the desired flux rate. For each path length of the phantom, an associated, respective count rates for the respective bins as registered at an arbitrary detector pixels is then stored. As a refinement of this, different sets of calibration data may be acquired for each pixel or at least for different pixel groups (regions) of the detector D. In other words, one measures, for a given pixel, per energy bin a different count rate-versus-path length curve by varying the path length. The calibration phantom may have a stepped profile to realize the different path lengths or one uses a set of different phantom blocks having different heights. In one embodiment, the phantom body is formed from a suitable thermoplastic such as Polyoxymethylene (e.g., Dekin® or other). However, other suitable calibration phantom materials are also envisaged herein such as Poly(methyl methacrylate)(PMMA), Polyoxymethylene (POM), Teflon® or others. Preferably, the phantom material should match the spectral attenuation properties of human soft tissue as close as possible. In particular, the phantom body material is so chosen so as to correspond to the spectral attenuation properties of water.

The measured curves for each bin and phantom path length may be stored efficiently in an array data structure, pointer structure, or other. However, other ways of encoding the count-versus-path length curves are also envisaged. For instance, in other embodiments the curves may be stored as explicit functional relationships obtained by using any suitable numerical approximation technique such as polynomial, splines, etc., to fit the discrete path length data points to associated count rates obtained in the calibration. In particular, the calibration curves $c_i$ may be stored in a look-up table (LUT) or other.

The proposed path length converter PLC as used herein is configured to overcome the ambiguity due to non-injectivity of the calibration curves. This is achieved by converting into a respective path length for a given bin, not only based on the calibration curve for that given bin but also based on at least one (or more) additional curve for another bin. This additional, "auxiliary" calibration curve may be that of another energy bin for the same pixel but any other calibration curve in the calibration data may be used. In one preferred embodiment, all the available curves from all available bins are used when computing the path length for a given pixel position. To compute the path length, the path length convertor performs a minimization operation by minimizing the mismatch between the measured count rates and the expected count rates as predicted by the calibration curves of all bins. The fit can be quantified by formulating an objective function that combines the knowledge about the "mismatches" between i) the measured count rates and ii) the count rates as per the two or more calibration curves. The objective function is then optimized in terms of the associated path length as per the calibration curves for more than two (in particular all bins) that best fits or "explains" the measured counts Π. A misfit is represented by the value of the objective function and it is the goal to minimize said misfit. Exemplary embodiments include least square sums (see eq(1) discussed further below), probabilistic methods such as maximum likelihood or others. Any numerical optimization algorithm such as Newton Raphson or other can be used to solve the objective function for the sought after path length to achieve the conversion.

The non-injectivity of the calibration curves of individual bins used herein does as such not admit to a straightforward conversion by inversion as for the case of non-injective calibration curves (e.g. FIG. 3a). But Applicant has recognized that this is only an apparent disadvantage. Because of the non-injectivity of some of the calibration curves c, an enlarged number of measurements are required to resolve the ambiguity with respect to the estimated path length, by using counts in several bins at the same time. It has been observed that this multi-bin-use makes the proposed path length conversion robust against noise. In addition, as mentioned above, the spectral performance is improved. This is to be contrasted with the alternative design choice for small pixel size which allows having one-to-one behavior also at the most critical pixel points on the sinogram (the "hottest points"). We propose herein not to follow this paradigm, because in this "one-to-one" approach one deliberately sacrifices spectral performance even on most parts of the sinogram where image information is hidden, that is, along rays/locations through the patient where the rate performance is very small.

Figures 5A, 5B:
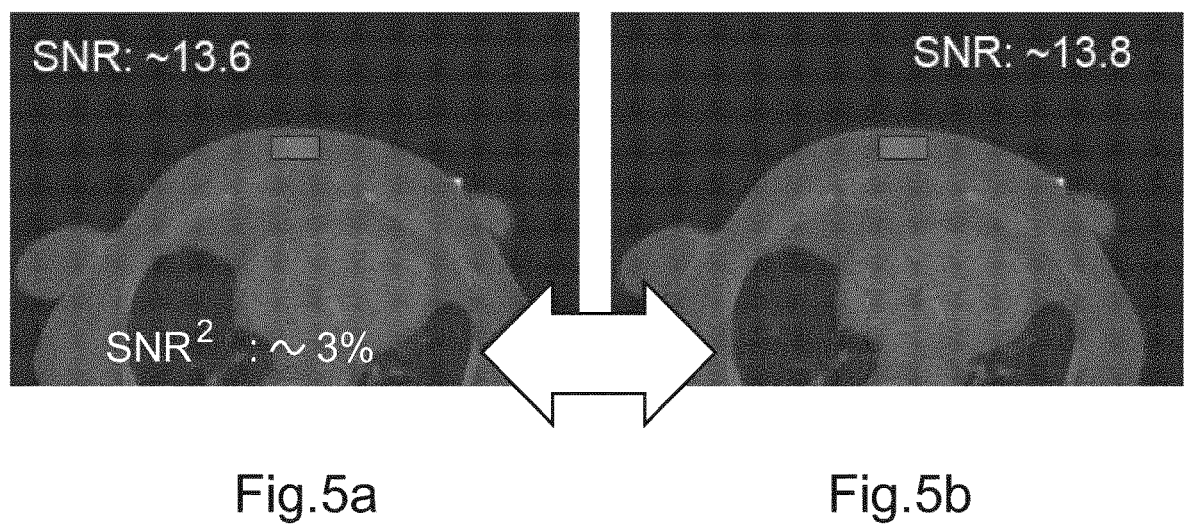
FIG. 5 shows noise data in imagery obtained by the proposed image signal processing system.

That the proposed system also delivers a reasonable rate performance not significantly impacted by higher noise levels is shown in the exemplary imagery in FIG. 5. The imagery has been obtained in a simulation study based on a phantom. More particularly, FIG. 5 illustrates an increase in image noise as a function of pixel size, with small size in FIG. 5*a* versus larger pixel size in FIG. 5*b*. The gain in spectral performance (not shown in this disclosure) significantly outweighs this very slight noise increase of mere 3%. FIG. 5 illustrates that only in the peripheral areas of the phantom one can measure an increase in image noise that is attributable to larger pixel pitch (and hence to faster degradation of the DQE with photon flux). In other words, the study illustrates an only marginal effect on image noise, in an area that is of little diagnostic relevance.

Figure 6:
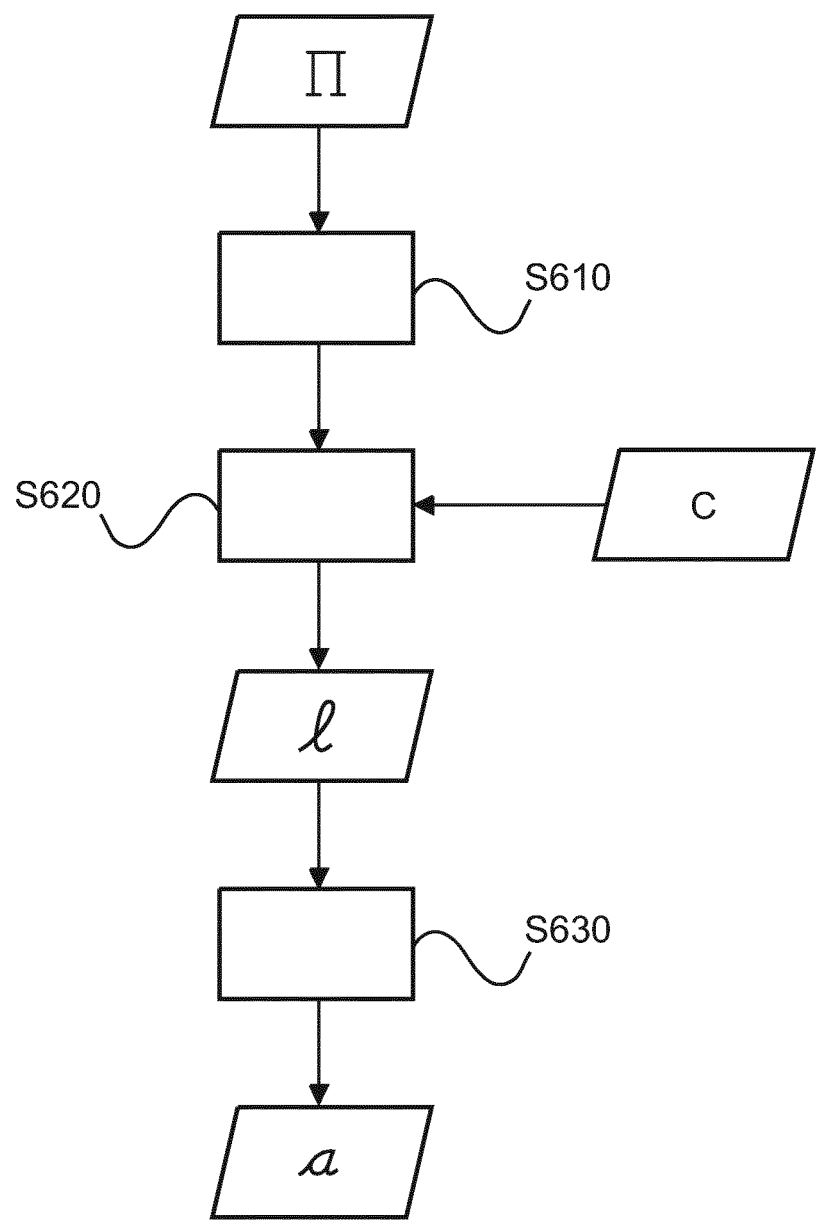
FIG. 6 shows a flow chart of an image signal processing method.

Reference is now made to FIG. 6 which shows a flow chart of image signal processing method that can be implemented by the proposed path length converter PLC. It will be understood however, that the proposed method as described below can also be understood in its own right and is not necessarily tied to the architecture of FIG. 4 above.

At step S610 projective photon counting data Π as acquired with a photon counting detector system D, PCT of an x-ray imaging apparatus IA is received. This data may comprise photon counting data from a single direction or may comprise photon counting projection data obtained from a plurality of directions such as in CT or other rotational x-ray systems (C-arm).

At step S620 the photon count rate in the projection data is then converted into respective path lengths based on calibration data. The path lengths may be designated in any suitable length dimension. The conversion operation at step S620 converts, for a given detector pixel position and for a given respective energy bin, the respective photon count rate entry in Π into a respective path length $\ell$. The conversion is repeated for each detector pixel position and each bin to so obtain a collection of path lengths. If applicable, this step is also repeated for each projection direction such as in CT.

The collection of path lengths (of applicable from different projection directions) may then be reconstructed at step S630 into image elements of a cross-section image.

The calibration data as used in step S620 includes, for different energy bins, respective photon counting versus path length curves that have been obtained in a previous calibration procedure using an X-ray imaging apparatus having a photon counting detector system D, PCT. For instance, the calibration procedure may be performed for a detector of a certain type and the so obtained calibration data can then be used in other imaging apparatus having the same type of detector. Preferably however the calibration procedure is done individually for each detector or imager. Alternatively to performing an experimental calibration procedure, the calibration curves may be derived from a signal model using in particular probabilistic methods, on which more below when describing FIG. 6.

It should be noted that in one embodiment there is a further step of correcting the non-linear calibration curves for pile-up effects of the individual bins once we estimated the path-length, ie, once we know the flux. From the so corrected data we can then derive material decompositions as if the bins were not subject to pile-up.

The pixel size relative to the flux rate in the imager is deliberately configured in such a way that at least one, more or all of the recorded calibration curves for the different energy bins might show none-one-to-one behavior. In other words, the curved are not uniquely invertible in the classical sense on a bin-by-bin level, but this is accepted herein because it allows increasing spectral performance for the majority of points in the sinogram without giving away too much rate performance.

The proposed conversion step at step S620 can cope with this ambiguity by using, for given pixel position and bin, two or more calibration curves: the one for the given bin and one other curve of one of the other bins of the same pixel.

In one embodiment only two curves are used for the conversion but preferably more than two, in particular all available curves from all bins are used at once for a given path length conversion. The observed count rates are fitted to the count rates as per the calibration data.

Figure 7:
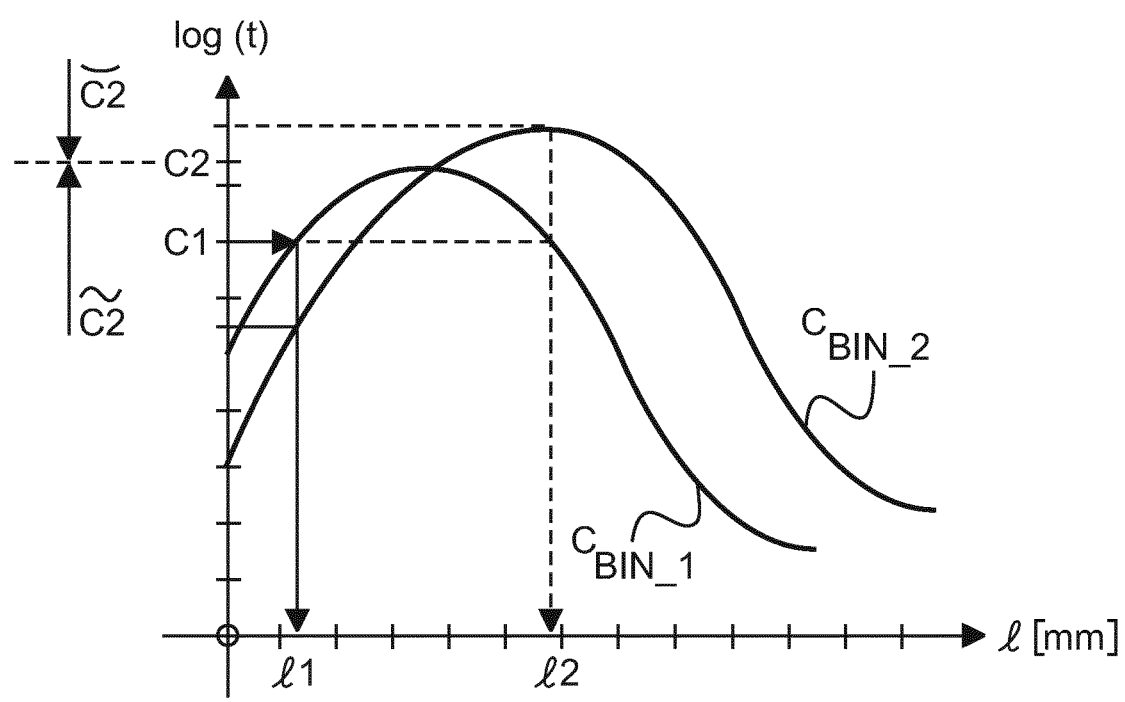
FIG. 7 is an illustration of an embodiment of an image signal processing method of FIG. 6.

A simple embodiment is illustrated in FIG. 7. For ease of representation, only two calibration curves $c_{BIN\_1}$, $c_{BIN\_2}$ for two different energy bins BIN_1 and B2 are shown. Suppose then that in bin BIN_1 a certain count rate C1 is detected when imaging an object of interest (e.g., a human patient or animal). A look-up operation based on the calibration curve $c_{BIN\_1}$ for this BIN_1 then yields two possible path lengths for the conversion, namely $\ell_1$ or $\ell_2$. This ambiguity is the result of the curve being not one-to-one. It is proposed herein then to use a second, in particular a neighboring curve BIN_2 for the other bin BIN_2 to resolve this ambiguity. As shown in FIG. 7, this second, auxiliary calibration curve has its maximum at a different location on the path length axis. Using the two estimates or "candidate" path lengths $\ell_1$ or $\ell_2$ from the first curve $c_{BIN\_1}$, we can now compute/look-up in calibration curve $c_{BIN\_2}$ two predicted count rates $\widetilde{C2}$ and $\widetilde{C2}$. The deviations of the predicted count rates from the actually measured rate C2 in the other bin BIN_2 are then compared. The algorithm then returns the one of the two path lengths $\ell_1$ or $\ell_2$, whose predicted count under $c_{BIN\_2}$ is closest to the actually registered count rate C2 in the auxiliary bin BIN-2. It should be clear, that this fitting procedure can be reversed by starting from the C2 reading in bin BIN_2 and then obtaining an estimate for the path length by using the calibration curve for BIN_1 and the count C1 as the decider.

It will be observed that the method as per FIG. 7 may yield an inferior result in the presence of high noise contributions. It is therefore proposed herein advanced embodiments of FIG. 7, where information from all the remaining bins (and not only from two bins) is used. For instance, in one refinement of the approach in FIG. 7, one sets at least one the thresholds in the PCT so high, that at least one of the calibration curves is one-to-one. The conversion for the related bin is then straightforward and one may then program the convertor PLC to use the bin with the one-to-one calibration curve as the decider for all other bins so as to achieve yet better noise robustness.

In a further refinement of the approach of FIG. 7, the rationale in FIG. 7 of seeking a "close" match across other bins may be formulated in terms of an objective function such as a least square sum over a plurality (in particular all) bins to so optimize the accumulated match with the measured count data across the bins. The objective function may then be optimized to so effect the conversion into the desired path length.

In more detail, assuming that calibration curves $c(\ell)$ (with i denoting the bins) are given, at least one or all being non-monotonic similar to FIG. 3(*b*). It is then possible to convert photo counts into an effective length $\ell$ of calibration material D, given a set of M (e.g., M=3 as in the example of FIG. 3(b) above) measured numbers of counts mi for each energy thresholds $U_1 \ldots U_M$ of the energy-sensitive photon counting detector. The conversion can be achieved by a fitting operation, e.g. by using a least-squares approach minimizing the following objective function with respect to the $\ell$ effective thickness of a calibration material D:

$$\chi^2(m_i, \ell) = \Sigma_{i=1}^{M}(m_i - c_i(\ell))^2 \qquad \text{eq (1)}$$

The objective function as per eq (1) can be refined into the following $$\chi^2(m_i, \ell) = \sum_{i=1}^{M}\left(\frac{m_i - c_i(\ell)}{\sigma_i^2(\ell)}\right)^2 \qquad \text{eq(1a)}$$

where the objective functions now include components such as noise variances $\sigma_i^2(\ell)$ etc. to account for the image noise caused by the detector module. The formulation via eq (1a) can be used to enforce low noise path length $\ell$ solutions. Similarly to the c(.) curves, estimates for the variances can be obtained in a calibration procedure where measurements are taken for a given pixel position a number of times and these measurement are then combined in the $2^{nd}$ sample central moment formula to obtain an estimate for the variance. Alternatively to taking calibration measurements, the noise estimates may be computed from a signal model.

After the estimation of the path length $\ell$ by minimizing eqs (1) or (1a), the ambiguity inherent of each of the outputs of all bins is resolved. A conventional reconstruction of the D values for all readings on the sinogram can then be performed to yield an image free or at least with reduced artifacts due to pileup.

Alternatively, in case the joint probability density function (pdf) of the measured data is known for each of the thresholds $U_1 \ldots U_M$, a likelihood maximization approach can be used to effect the path length conversion. This approach requires in general a forward signal model for the pile-up effect from which the pdfs of the observed counts can be derived from the incident counts. In one embodiment, independent Poisson pdfs are used for the counts registered in two-sided energy bins to model the counts, neglecting the effects of pileup on the statistics. In case one-sided bins are used, the assumption of statistical independence no longer holds, the co-variances have to be taken into account when formulating the pdf. According to one embodiment, a pile-up model as described by E Roessl et al in "Fourier approach to pulse pile-up in photon-counting x-ray detectors", Med. Phys. 43, pp 1295 (2016) is used but other models are not excluded herein.

More generally, objective functions other than least square sum eqs (1),(1a) may be used instead and this is then optimized for the least value. The object function includes in general functional components $\|m_i - c_i(\ell)\|$ that quantify, in a suitable norm $\|.\|$, the miss-match between the projection data as actually counted m and the photon counting events to be expected $c_i(\ell)$ from the calibration curves. These functional components $\|m_i - c_i(\ell)\|$ are combined by the objective function into a suitable scalar value ($\|.\|$) to quantify the overall cost of the miss-matches.

It should be noted that in the above mentioned look-up and fitting operations involved in the path length conversion, there are preferably interpolation steps performed to interpolate on the path length axis between the measured sample path lengths from the calibration procedure. The proposed method and system is therefore not confined to the discrete space as per the calibration but can operate on the path length axis as if it were continuous. However this does not excludes simpler embodiments, where the path length conversion is performed discretely, that is, where the conversion is confined to the discrete sample path lengths of the calibration.

Thanks to the proposed method and system, the X-ray source 212 of the imager is operable during object imaging at a photon flux rate so that a reciprocal of the flux-rate is approximately equal to or exceeds significantly (about 3-about 5 times) the inverse of the dead-time of the detector unit D. In other words, the imager can be operated beyond the flux rate that corresponds to the paralyzable output maximum of registered counts of individual energy thresholds/bins.

It should be noted above that the calibration data in general also includes photon counting data collected in air scans. An air scan is one where there is no object present in the examination region. This air scan data is then used and compared with the projection data whilst an object of interest resides in the imaging region. The above described path length conversion is then carried for the projection data collected in the air scan as well as for the projection data collected in the object scan. The so obtained path lengths from the two scans are then compared to so derive attenuation data which is then reconstructed in a re-constructer RECON into the cross sectional image. The components of the image processing system ISP may be implemented as software modules or routines in a single software suit and run on a general purpose computing unit PU such as a workstation associated with the imager IM or a server computer associated with a group of imagers. Alternatively the components of the image processing system ISP may be arranged in a distributed architecture and connected in a suitable communication network.

Alternatively some or all components may be arranged in hardware such as a suitably programmed FPGA (field-programmable-gate-array) or as hardwired IC chip on a PCB module included into the circuitry for the detector D system.

Although in the above, the convertor converts into effective material path length $\ell$, this should be considered broadly, as converting into any other parameter that is equivalent to said effective path length is also envisaged herein. Furthermore, in relation to any of the above mentioned formulae, mathematically equivalent re-formulations of these are also envisaged herein.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention. This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image signal processing system, comprising:
   an input interface for receiving photon counting projection data acquired by an X-ray imaging apparatus having a photon counting detector;
   a calibration data memory holding calibration data, said calibration data encoding photon counting data versus path lengths curves for different energy thresholds of said detector, at least one of said curves being non-injective; and
   a path length convertor configured to convert an entry in said photon counting projection data into an associated path length based on at least two photon counting data versus path lengths curves encoded in said calibration data, wherein the path length conversion comprises computing at least two estimates for the associated path length based on one of the at least two curves and choosing one of the two estimates as the associated path length based on at least one other of the curves and photon counting projection data for at least one other threshold.

2. The image signal processing system of claim 1, with said calibration data previously detected in a calibration procedure or said calibration data set derived from a signal model.

3. The signal processing system of claim 1, comprising:
   an image reconstructor configured to reconstruct, based at least on the converted path length, an image element of an image.

4. The signal processing system of claim 1, where the path length convertor operates to fit said entry of the photon counting projection data to photon counting data as per at least two of said curves.

5. The signal processing system of any one of the claim 1, wherein the path length convertor is configured to convert into the associated path length by optimizing an objective function, said objective function being dependent on a deviation between the projection data and photon counting data as per the curves.

6. The signal processing system of claim 5, wherein the objective function includes a least squares sum.

7. The signal processing system of claim 5, wherein the objective function includes a likelihood function based on a probability density function for the photon counting data.

8. The signal processing system of claim 5, wherein the objective function incorporates a noise modelling component configured to model for noise behavior of the detector or for the different detector.

9. An X-ray imaging apparatus comprising a signal processing system of claim 1.

10. A signal processing method, comprising:
    receiving photon counting projection data acquired by an X-ray imaging apparatus having a photon counting detector; and
    converting an entry in said photon counting projection data into an associated path length based on calibration data, said calibration data encoding photon counting data versus path lengths curves for different energy thresholds of said detector, at least one of said curves being non-injective, wherein the converting is based on at least two photon counting data versus path lengths curves encoded in said calibration data; and wherein the path length conversion comprises computing at least two estimates for the associated path length based on one of the at least two curves and choosing one of the two estimates as the associated path length based on at least one other of the curves and photon counting projection data for at least one other threshold.

11. The signal processing method of claim 10, comprising:
    reconstructing, based at least on the converted path length, an image element of an image.

12. A non-transitory computer-readable medium for storing executable instructions, which when executed by at least one processor, cause the at least one processor to perform a signal processing method comprising:

receiving photon counting projection data acquired by an X-ray imaging apparatus having a photon counting detector; and converting an entry in said photon counting projection data into an associated path length based on calibration data, said calibration data encoding photon counting data versus path lengths curves for different energy thresholds of said detector, at least one of said curves being non-injective, wherein the converting is based on at least two photon counting data versus path lengths curves encoded in said calibration data; and wherein the path length conversion comprises computing at least two estimates for the associated path length based on one of the at least two curves and choosing one of the two estimates as the associated path length based on at least one other of the curves and photon counting projection data for at least one other threshold.

* * * * *